(12) United States Patent
Fey

(10) Patent No.: US 6,566,523 B1
(45) Date of Patent: May 20, 2003

(54) METHOD FOR THE ENANTIOMER SEPARATION OF CIS-8-BENZYL-7,9-DIOXO-2,8-DIAZABICYCLO[4.3.0]NONANE

(75) Inventor: Peter Fey, Wuppertal (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/018,110

(22) PCT Filed: Jun. 5, 2000

(86) PCT No.: PCT/EP00/05116

§ 371 (c)(1),
(2), (4) Date: Dec. 14, 2001

(87) PCT Pub. No.: WO00/76996

PCT Pub. Date: Dec. 21, 2000

(30) Foreign Application Priority Data

Jun. 16, 1999 (DE) .......................... 199 27 412

(51) Int. Cl.[7] ...................... C07D 471/04; C07D 487/02
(52) U.S. Cl. ........................ 546/113; 546/112
(58) Field of Search .................. 546/113, 112

(56) References Cited

U.S. PATENT DOCUMENTS

| 3,682,925 | A | 8/1972 | Den Hollander et al. ... 260/285 |
|---|---|---|---|
| 5,059,597 | A | 10/1991 | Petersen et al. .......... 514/224.5 |
| 5,416,096 | A | 5/1995 | Petersen et al. ............ 514/312 |
| 5,607,942 | A | 3/1997 | Petersen et al. ............ 546/200 |
| 6,392,044 | B1 * | 5/2002 | Diehl et al. ................. 546/113 |

FOREIGN PATENT DOCUMENTS

| CA | 2086914 | 7/1993 |
|---|---|---|
| EP | 0550903 | 7/1993 |
| WO | 9313087 | 7/1993 |

* cited by examiner

Primary Examiner—Alan L. Rotman
Assistant Examiner—Rita Desai
(74) Attorney, Agent, or Firm—Jerrie Chiu

(57) ABSTRACT

The invention relates to a method for the enantiomer separation of cis-8-benzyl-7,9-dioxo-2,8-diazabicy-clo[4.3.0]nonane (also described below as cis-6-benzyl-5,7-dioxooctahydropyrrolo[3,4-b]pyridine or dioxopyrrolopiperidine). The invention also relates to a method for producing (1S, 6R)- and (1R, 6S)-8-benzyl-7,9-dioxo-2,8-diazabicyclo[4.3.0]nonane using the above method. The invention further relates to the (−)-2,3:4,6-di-O-isopropylidene-2-keto-L-gulonic acid salts of (1S, 6R)- and (1R, 6S)-8-benzyl-7,9-dioxo-2,8-diazabicyclo[4.3.0] nonane and to a method for producing the same. Finally, the invention relate to a method for the enantiomer enrichment of (1S, 6R)-8-benzyl-7,9-dioxo-2,8-diazabicyclo[4.3.0]-nonane.

10 Claims, No Drawings

METHOD FOR THE ENANTIOMER SEPARATION OF CIS-8-BENZYL-7,9-DIOXO-2,8-DIAZABICYCLO[4.3.0]NONANE

The present invention relates to a process for the separation of enantiomers of cis-8-benzyl-7,9-dioxo-2,8-diazabicyclo[4.3.0]nonane (also called cis-6-benzyl-5,7-dioxooctahydropyrrolo[3,4-b]pyridine or dioxopyrrolopiperidine below). In a further aspect, the invention relates to a process for the preparation of (1S,6R)- and (1R,6S)-8-benzyl-7,9-dioxo-2,8-diazabicyclo[4.3.0]nonane using the aforementioned process. The invention furthermore relates to the (−)-2,3:4,6-di-O-isopropylidene-2-keto-L-gulonic acid salts of (1S,6R)- and (1R,6S)-8-benzyl-7,9-dioxo-2,8-diazabicyclo[4.3.0]nonane, and to a process for their preparation. The invention further relates to a process for the enrichment of enantiomers of (1S,6R)-8-benzyl-7,9-dioxo-2,8-diazabicyclo[4.3.0]nonane.

(1S,6R)-8-benzyl-7,9-dioxo-2,8-diazabicyclo[4.3.0]nonane of the formula (Ia)

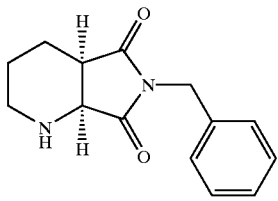

(Ia)

is a valuable intermediate for the preparation of (S,S)-2,8-diazabicyclo[4.3.0]nonane:

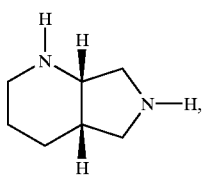

to which it can be converted by reduction of the carbonyl groups and debenzylation in a manner known per se (EP-A-0350733). (S,S)-2,8-Diazabicyclo[4.3.0]nonane, for its part, is used for the preparation of the antibiotic moxifloxacin (INN):

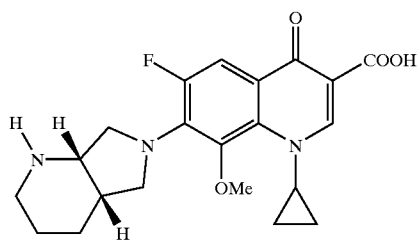

1-Cyclopropyl-7-([S,S]-2,8-diazabicyclo[4.3.1]non-8-yl)-6-fluoro-1,4-dihydro-8-methoxy-4-oxo-3-quinolonecarboxylic acid (moxifloxacin) (EP-A-0350733).

The enantiomer

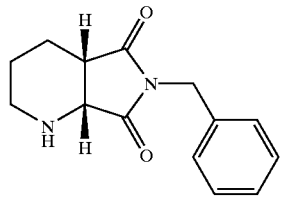

(Ib)

is also a valuable intermediate for the preparation of (R,R)-2,8-diazabicyclo-[4.3.0]nonane:

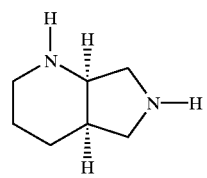

which, for its part, can be used for the preparation of very active antibacterial agents (e.g. Interscience Conference on Antimicrobial Agents and Chemotherapy (ICAAC), 1996, Abstr. No. F-001).

There was therefore the desire for an inexpensive process for the preparation of (1S,6R)-8-benzyl-7,9-dioxo-2,8-diazabicyclo[4.3.0]nonane and of (1R,6S)-8-benzyl-7,9-dioxo-2,8-diazabicyclo[4.3.0]nonane from racemic cis-8-benzyl-7,9-dioxo-2,8-diazabicyclo[4.3.0]nonane, which is obtained by nuclear hydrogenation of pyridine-2,3-dicarboxylic acid N-benzylimide as described in EP-A-0 350 733 (Example K).

EP-A-0 550 903 discloses a process for the resolution of cis-8-benzyl-7,9-dioxo-2,8-diazabicyclo[4.3.0]nonane using tartaric acid (Example A, Method IV and Example B, Method IIa)). For the preparation, for example, of the (1S,6R) enantiomer, the processes described there necessitate the repeated recrystallization of the diestereomeric D-(−)-tartaric acid salts or reaction with L-(+)-tartaric acid and subsequent reaction of the released mother liquor with D-(−)-tartaric acid and recrystallization. The enantiomeric excesses obtained are inadequate at 93.8% ee for the (1R,6S) enantiomer and 96.6% ee for the (1S,6R) ehantiomer. The process suffers from the disadvantage that the provision of the desired enantiomer in adequate purity necessitates lengthy operations. The process is therefore unsuitable for the production of (1S,6R)-8-benzyl-7,9-dioxo-2,8-diazabicyclo[4.3.0]nonane on the industrial scale.

The object of the present invention therefore consisted in making available a process for the enrichment of enantiomers of cis-8-benzyl-7,9-dioxo-2,8-diazabicyclo[4.3.0]nonane, using which (1S,6R)-8-benzyl-7,9-dioxo-2,8-diazabicyclo[4.3.0]nonane or (1R,6S)-8-benzyl-7,9-dioxo-2,8-diazabicyclo[4.3.0]nonane can be made available inexpensively in large amounts and with the required purity.

The inventor therefore undertook intensive investigations to solve the problems of resolution using cis-8-benzyl-7,9-dioxo-2,8-diazabicyclo[4.3.0]nonane. In the course of this, various chiral acids known in the prior art were investigated for their suitability in solving the objects described above. It was shown here that numerous chiral acids mentioned in the prior art for the resolution of amines were unsuitable for achieving the objective. Finally, in a completely surprising manner, an economical process for the enrichment of enantiomers of cis-8-benzyl-7,9-dioxo-2,8-diazabicyclo[4.3.0]

nonane was found, which uses (-)-2,3:4,6-di-O-isopropylidene-2-keto-L-gulonic acid or (1S)-(+)-camphor-10-sulfonic acid or (1R)-(-)-camphor-10-sulfonic acid as a chiral acid. (-)-2,3:4,6-Di-O-isopropylidene-2-keto-L-gulonic acid is known per se for the resolution of amines (US-A-3,682,925). However, it has surprisingly been shown that when using these specific chiral acids (1S,6R)-8-benzyl-7,9-dioxo-2,8-diazabicyclo[4.3.0]nonane and (1R,6S)-8-benzyl-7,9-dioxo-2,8-diazabicyclo[4.3.0]nonane can be obtained inexpensively in a few steps with high purity in a particularly simple manner.

The invention thus relates in one embodiment of the invention to a process for the enrichment of enantiomers of cis-8-benzyl-7,9-dioxo-2,8-diazabioclo[4.3.0]nonane, that comprises the reaction of mixtures of enantiomers of cis-8-benzyl-7,9-dioxo-2,8-diazabicyclo[4.3.0]nonane of the formula (I)

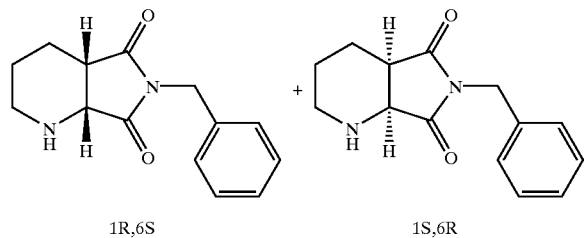

(I)

1R,6S             1S,6R with (-)-2,3:4,6-di-O-isopropylidene-2-keto-L-gulonic acid or its hydrates of the formula (II):

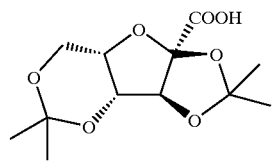

(II)

Enrichment of enantiomers here means that the molar ratio of one enantiomer to the other is increased as far as complete separation of enantiomers. The mixture of enantiomers of cis-8-benzyl-7,9-dioxo-2,8-diazabicyclo[4.3.0] nonane includes any desired mixtures of the enantiomers and is not restricted to the racemate (1:1 mixture). Thus mixtures of (1S,6R)- and (1R,6S)-8-benzyl-7,9-dioxo-2,8-diazabicyclo[4.3.0]nonane in the molar ratio of, for example, 80:20 to 20:80 can be employed.

The reaction of the mixture of enantiomers with (-)-2,3:4,6-di-O-isopropylidene-2-keto-L-gulonic acid is carried out in solution or suspension. As solvents, organic solvents or mixtures thereof with up to 20% by weight of water can be employed. These organic solvents are preferably selected from the group which consists of alcohols (e.g. methanol, ethanol, n-propanol, isopropanol, isobutaiol, n-butanol and sec-butanol), ketones (e.g. acetone, methyl ethyl ketone, methyl isobutyl ketone) and ethers (such as, for example, tetrahydrofuran, dimethoxyethane), acetonitrile, ethyl acetate, toluene, dimethylformamide. Mixtures of the organic solvents can also be used. Ketones are preferred, particularly preferably methyl ethyl ketone.

The mixture of enantiomers and the (-)-2,3:4,6-di-O-isopropylidene-2-keto-L-gulonic acid can be mixed together in any desired manner. Expediently, they can be mixed together, however, by adding, for example, the acid dissolved or suspended in the respective solvent to a solution or suspension of the mixture of enantiomers. The addition is carried out at room temperature (20° C.) or elevated temperature of up to approximately 110° C. The mixture of enantiomers and the (-)-2,3:4,6-di-O-isopropylidene-2-keto-L-gulonic acid are preferably reacted at elevated temperature from 60 to 110° C., preferably at the boiling temperature of the respective solvent. The reaction can optionally also be carried out under pressure. The reaction of the amines with the acids takes place spontaneously per se. However, it can be expedient to carry out the reaction for a longer period of time of approximately 10 minutes up to a number of hours (e.g. at most 20 hours, preferably approximately up to 2 hours), since as a result of redissolution processes of the two diastereomeric salts an enrichment of one of the two diastereomeric salts can take place under the given conditions (temperature, solvent).

The molar ratio of the racemic amine and the acid is expediently 1:0.4 to 1:1. The molar ratio of the racemic amine and of the acid is preferably 1:0.4 to 1:0.6 and the molar ratio is particularly preferably approximately 1:0.5. The reason why the reaction is preferably carried out with a molar deficit of the acid consists in the fact that the (1R, 6S)-8-benzyl-7,9-dioxo-2,8-di azabicyclo[4.3.0]nonane-(-)-2,3:4,6-di-O-isopropylidene-2-keto-L-gulonic acid salt preferably precipitates. The (1S,6R)-8-benzyl-7,9-dioxo-2,8-diazabicyclo[4.3.0]nonane enantiomer and the corresponding gulonic acid salt remain in solution. Since the desired product is the free (1S,6R) amine, the complete reaction thereof to the gulonic acid salt for the separation of the other enantiomer is not necessary and economically also not desirable.

After the reaction, the reaction mixture is cooled to the filtration temperature of, for example, 5° C. to 40° C. The filtration temperature is chosen such that the desired diastereomeric salt is obtained in maximum yield and purity.

In the process of the invention, as a rule, as described above, the(1R,6S)-8-benzyl-7,9-dioxo-2,8-diazabicyclo [4.3.0]nonane-(-)-2,3:4,6-di-O-isopropylidene-2-keto-L-gulonic acid salt first precipitates, and is isolated in high purity by filtration. By recrystallizing once, the salt can be obtained in virtually diastereomerically pure form. The free amine can be obtained from the salt by reaction with bases in a manner known per se.

The unreacted (1S,6R)-8-benzyl-7,9-dioxo-2,8-diazabicyclo[4.3.0]nonane and the (-)-2,3:4,6-di-O-isopropylidene-2-keto-L-gulonic acid salt thereof as a rule remain in solution. The salt can be crystallized from the solution by further cooling, or the free amine can be obtained directly by reaction with bases and isolated by enrichment.

Using the process for the separation of enantiomers described above, mixtures of the formula (1) which contain a molar excess of one of the two enantiomers can generally be prepared and reused in a suitable manner.

The process of the invention is suitable as described above for the preparation of (1S,6R)-8-benzyl-7,9-dioxo-2, 8-diazabicyclo[4.3.0]nonane of the formula (Ia)

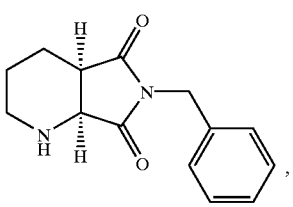

(Ia)

and for the preparation of (1R,6S)-8-benzyl-7,9-dioxo-2,8-diazabicyclo[4.3.0]nonane of the formula (Ib)

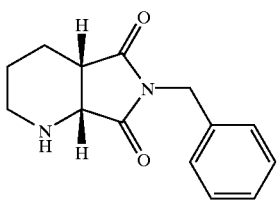

(Ib)

In the process of the invention, the release of the amines from the (−)-2,3:4,6-di-O-isopropylidene-2-keto-L-gulonic acid salts is preferably carried out using bases. The release of the amines is preferably carried out using a base which is selected from the group which consists of sodium hydrogencarbonate and ammonia.

The invention thus also relates to (1S,6R)-8-benzyl-7,9-dioxo-2,8-diazabicyclo[4.3.0]nonane-(−)-2,3:4,6-di-O-isopropylidene-2-keto-L-gulonic acid salt of the formula

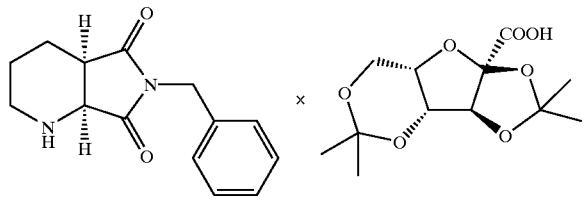

and (1R,6S)-8-benzyl-7,9-dioxo-2,8-diazabicyclo[4.3.0]nonane-(−)-2,3:4,6-di-O-isopropylidene-2-keto-L-gulonic acid salt of the formula

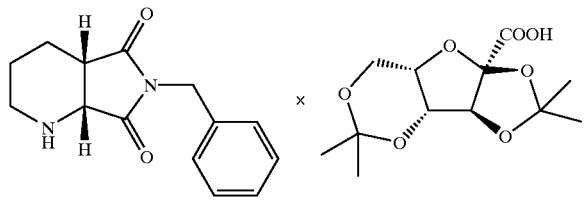

which are obtained as novel intermediates in the process and from which the corresponding amines can be isolated in a simple manner. Mixtures of (1R,6S)- and (1S,6R)-8-benzyl-7,9-dioxo-2,8-diazabicyclo[4.3.0]nonane-(−)-2,3:4,6-di-O-isopropylidene-2-keto-L-gulonic acid salts can also be obtained by the process of the invention and optionally processed further.

The invention furthermore relates to a process for the enrichment of enantiomers of (1S,6R)-8-benzyl-7,9-dioxo-2,8-diazabicyclo[4.3.0]nonane of the formula (Ia)

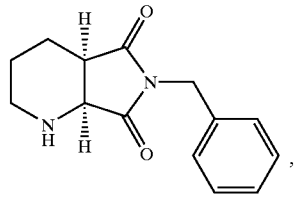

(Ia)

which comprises the reaction of a solution of a mixture of enantiomers of cis-8-benzyl-7,9-dioxo-2,8-diazabicyclo[4.3.0]nonane of the formula (I) in which a molar excess of (1S,6R)-8-benzyl-7,9-dioxo-2,8-diazabicyclo[4.3.0]nonane is present, it being possible for the mixture of enantiomers of cis-8-benzyl-7,9-dioxo-2,8-diazabicyclo[4.3.0]nonane to be wholly or partially present as a salt of a chiral acid, with hydrochloric acid.

In the process for the separation of enantiomers of cis-8-benzyl-7,9-dioxo-2,8-diazabicyclo[4.3.0]nonane, that comprises the reaction of mixtures of enantiomers of cis-8-benzyl-7,9-dioxo-2,8-diazabicyclo[4.3.0]nonane of the formula (I) with (−)-2,3:4,6-di-O-isopropylidene-2-keto-L-gulonic acid or its hydrates of the formula (II), a filtrate is obtained as described above in which an excess of (1S,6R)-8-benzyl-7,9-dioxo-2,8-diazabicyclo[4.3.0]nonane is present, which, depending on the ratio of the (−)-2,3:4,6-di-O-isopropylidene-2-keto-L-gulonic acid employed to the amine, can be present wholly or partially as a salt of (−)-2,3:4,6-di-O-isopropylidene-2-keto-L-gulonic acid. It has now been found in a completely surprising manner that if the solution enriched in this way with respect to the (1S,6R) enantiomer is treated with hydrochloric acid, virtually racemic cis-8-benzyl-7,9-dioxo-2,8-diazabicyclo[4.3.0]nonane hydrochloride precipitates, whereby virtually enantiomerically pure (1S,6R)-8-benzyl-7,9-dioxo-2,8-diazabicyclo[4.3.0]nonane or its hydrochloride remains in the solution. Obviously, the racemate of the hydrochloride has a higher tendency to crystallization than the hydrochloride of the enantiomerically pure (1S,6R)-8-benzyl-7,9-dioxo-2,8-diazabicyclo[4.3.0]nonane, which can be utilized for the further enrichment of the (1S,6R)-8-benzyl-7,9-dioxo-2,8-diazabicyclo[4.3.0]nonane. In principle, this process can also be employed in the case of solutions which are obtained from the reaction of other chiral acids, such as, for example, tartaric acid, with the racemic cis-8-benzyl-7,9-dioxo-2,8-diazabicyclo[4.3.0]nonane, and in which an excess is present with respect to one of the enantiomers.

In the process described above, the release of the (1S,6R)-8-benzyl-7,9-dioxo-2,8-diazabicyclo[4.3.0]nonane from its hydrochloride takes place with bases, the base preferably being selected from a group which consists of sodium hydrogencarbonate and ammonia.

The following scheme shows, by way of example, the process for the enrichment of enantiomers of the invention:

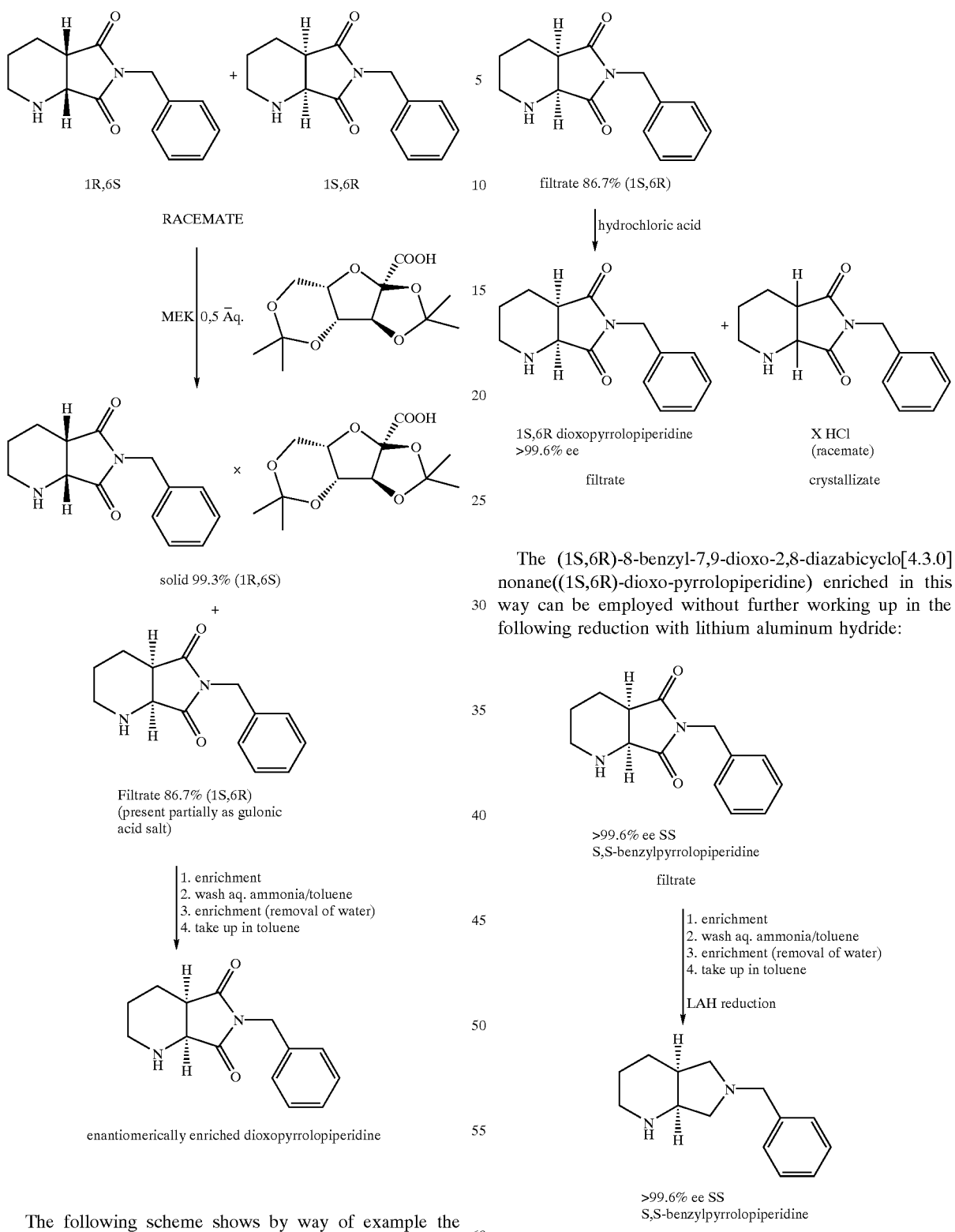

The following scheme shows by way of example the process for the enrichment of enantiomers of (1S,6R)-8-benzyl-7,9-dioxo-2,8-diazabicyclo[4.3.0]nonane by reaction of an mixture of enantiomers, in which a molar excess of (1S,6R)-8-benzyl-7,9-dioxo-2,8-diazabicyclo[4.3.0]nonane is present, with hydrochloric acid. In this process, the enantiomerically enriched filtrate obtained by the above reaction scheme is reacted with hydrochloric acid:

The (1S,6R)-8-benzyl-7,9-dioxo-2,8-diazabicyclo[4.3.0]nonane((1S,6R)-dioxo-pyrrolopiperidine) enriched in this way can be employed without further working up in the following reduction with lithium aluminum hydride:

In a further embodiment, the invention relates to a process for the enrichment of enantiomers of cis-8-benzyl-7,9-dioxo-2,8-diazabicyclo[4.3.0]nonane that comprises the reaction of mixtures of enantiomers of cis-8-benzyl-7,9-dioxo-2,8-diazabicyclo[4.3.0]nonane of the formula (I)

(I)

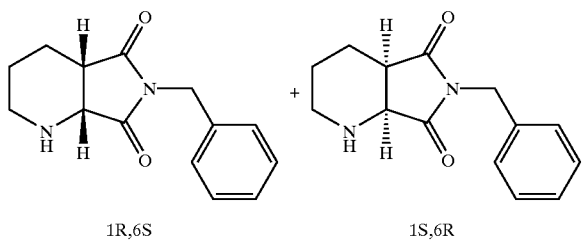

1R,6S           1S,6R with

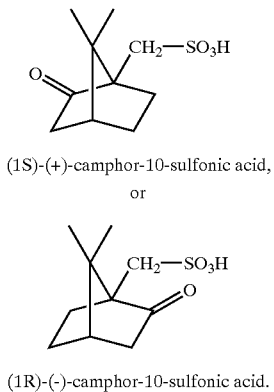

(1S)-(+)-camphor-10-sulfonic acid, or (1R)-(-)-camphor-10-sulfonic acid.

The meaning of the terms "enrichment of enantiomers" and "mixture of enantiomers" are the same as indicated above for the separation with (−)-2,3:4,6-di-O-isopropylidene-2-keto-L-gulonic acid.

The reaction of the mixture of enantiomers with the (1R or 1S)-camphor-10-sulfonic acid is carried out in solution or suspension. Organic solvents can be employed as solvents. These organic solvents are preferably selected from the group which consists of alcohols (e.g. methanol, ethanol, n-propanol, isopropanol, isobutanol, n-butanol and sec-butanol), ketones (e.g. acetone, methyl ethyl ketone, methyl isobutyl ketone) and ethers (such as, for example, tetrahydrofuran, dimethoxyethane), acetonitrile, ethyl acetate, toluene, dimethylformamide. Mixtures of the organic solvents can also be used. Acetonitrile, acetone and tetrahydrofuran are preferred.

The mixture of enantiomers and the (1R or 1S)-camphor-10-sulfonic acid can be mixed together in any desired manner. Expediently, however, they are mixed together by, for example, adding the acid dissolved or suspended in the respective solvent to a solution or suspension of the mixture of the enantiomers. The addition is carried out at room temperature (20° C.) or elevated temperature of up to approximately 110° C. The reaction of the mixture of enantiomers and of the (1R or 1S)-camphor-10-sulfonic acid is preferably carried out at elevated temperature of 60 to 110° C., preferably at the boiling temperature of the respective solvent. The reaction can optionally also be carried out under pressure. The reaction of the amines with the acids takes place spontaneously per se. However, it can be expedient to carry out the reaction for a longer period of time of approximately 10 minutes up to a number of hours (e.g. at most 20 hours, preferably approximately up to 2 hours), since as a result of redissolution processes an enrichment of one of the two diastereomeric salts can take place under the given conditions (temperature, solvent).

The molar ratio of the racemic amine and the acid is expediently 1:0.4 to 1:1. The molar ratio of the racemic amine and the acid is preferably 1:0.4 to 1:0.6 and the molar ratio is particularly preferably approximately 1:0.5.

After the reaction, the reaction mixture is cooled to the filtration temperature of, for example, 5° C. to 40° C. The filtration temperature is chosen such that the desired diastereomic salt is obtained in maximum yield and purity.

The release of the amines from the camphorsulfonic acid salts is preferably carried out using a base which is selected from the group which consists of sodium hydrogencarbonate and ammonia.

The invention further relates to (1S,6R)-8-benzyl-7,9-dioxo-2,8-diazabicyclo[4.3.0]nonane-(1S)-(+)-camphor-10-sulfonic acid salt of the formula

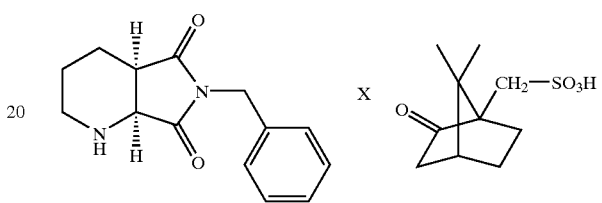

(1S,6R)-8-benzyl-7,9-dioxo-2,8-diazabicyclo[4.3.0] nonane-(1R)-(−)-camphor-10-sulfonic acid salt of the formula

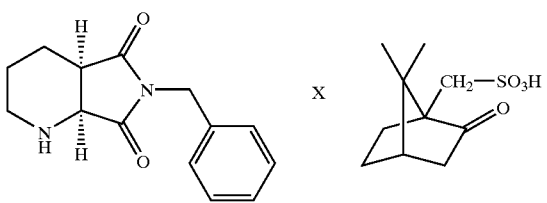

(1R,6S)-8-benzyl-7,9-dioxo-2,8-diazabicyclo[4.3.0] nonane-(1S)-(+)-camphor-10-sulfonic acid salt of the formula

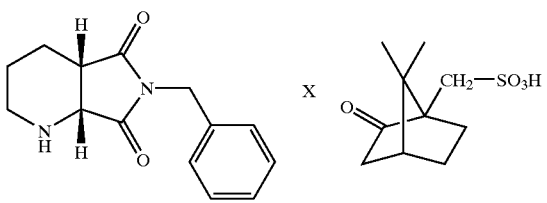

and the (1S,6R)-8-benzyl-7,9-dioxo-2,8-diazabicyclo[4.3.0] nonane-(1R)-(−)-camphor-10-sulfonic acid salt of the formula

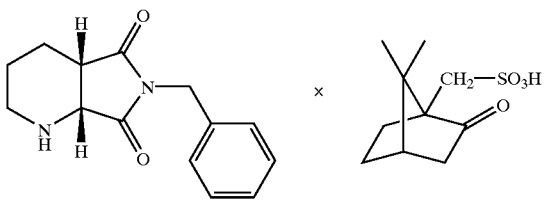

and mixtures of the amines with (1R or 1S)-camphor-10-sulfonic acid.

EXAMPLES

Example 1

Resolution of (1S,6R)- and (1R,6S)-8-Benzyl-7,9-dioxo-2,8-diazabicyclo-[4.3.0]nonane
Addition Variant A 2.0 kg (8.19 mol) of cis-8-benzyl-7,9-dioxo-2,8-diazabicyclo[4.3.0]nonane are suspended in 4.5 l (liters) of methyl ethyl ketone and heated to reflux temperature (83° C.). 1.2 kg of (−)-DAKS×$H_2O$ [(−)-2,3:4,6-di-O-isopropylidene-2-keto-L-gulonic acid monohydrate] and 1 g of seed crystals of (1R,6S)-8-benzyl-7,9-dioxo-2,8-diazabicyclo[4.3.0]nonane-(−)-2,3:4,6-di-O-isopropylidene-2-keto-L-gulonic acid salt are suspended in 4.0 l of methyl ethyl ketone (MEK). About ¼ of the suspension is pumped into the boiling cis-8-benzyl-7,9-dioxo-2,8-diazabicyclo[4.3.0]nonane solution, crystallization commencing. The mixture is stirred at this temperature for 30 min. The remaining suspension is added, then the suspension vessel and pump are rinsed with 500 ml of methyl ethyl ketone and the mixture is stirred under reflux for 1 h. It is cooled to room temperature, and the crystallizate is filtered off with suction and washed with 1.2 l of MEK. The crystals are dried overnight at 70° C. in vacuo.

Yield: 2037.1 g of (1R,6S)-8-benzyl-7,9-dioxo-2,8-diazabicyclo[4.3.0]nonane-(−)-2,3:4,6-di-O-isopropylidene-2-keto-L-gulonic acid salt, 86% enantiomeric excess (ee).

The combined filtrates are enriched in vacuo to give an oil, which slowly crystallizes.

Yield: 1196 g of (1S,6R)-8-benzyl-7,9-dioxo-2,8-diazabicyclo[4.3.0]nonane (crude product, which is present partially as (−)-2,3:4,6-di-O-isopropylidene-2-keto-L-gulonic acid salt).

146.2 g of this crude product are dissolved in 440 ml of toluene and treated with 32 ml of water.

5.1 ml of ammonia solution (25% strength) are added, the mixture is warmed to 40° C., the phases are separated and the organic phase is enriched in vacuo at 50° C.

Yield: 133.7 g of (1S,6R)-8-benzyl-7,9-dioxo-2,8-diazabicyclo[4.3.0]nonane 83.4% ee

Example 2

Resolution of (1S,6R) and (1R,6S)-8-Benzyl-7,9-dioxo-2,8-diazabicyclo[4.3.0]nonane
Addition Variant B 50 g (205 mmol) of cis-8-benzyl-7,9-dioxo-2,8-diazabicyclo[4.3.0]nonane are dissolved in 111 ml of methyl ethyl ketone (cloudy solution) and added dropwise in the course of 2 h to a boiling solution of 29.9 g of DAKS monohydrate in 114 ml of methyl ethyl ketone. The resulting suspension is stirred at boiling temperature for 10 min, cooled to room temperature and stirred at 20° C. for 2 h. The solid is filtered off with suction, washed with 30 ml of methyl ethyl ketone and dried in vacuo at 70° C.

Yield: 48.4 g of (1R ,6S)-8-benzyl-7,9-dioxo-2,8-diazabicyclo[4.3.0]nonane-(−)-2,3:4,6-di-O-isopropylidene-2-keto-L-gulonic acid salt, 92.2% ee.

The combined filtrates are enriched, dissolved in 50 ml of toluene and 6.3 ml of water and adjusted to pH 10 using about 1 ml of 25% strength ammonia solution. The phases are separated at 40° C., the organic phase is enriched and the residue is dried in vacuo.

Yield: 25.8 g of (1S,6R)-8-benzyl-7,9-dioxo-2,8-diazabicyclo[4.3.0]nonane 84.8% ee

Example 3

Resolution of (1S,6R)- and (1R,6S)-8-Benzyl-7,9-dioxo-2,8-diazabicyclo[4.3.0]nonane
Addition Variant C 200 g (819 mmol) of cis-8-benzyl-7,9-dioxo-2,8-diazabicyclo[4.3.0]nonane and 120 g (411 mmol) of DAKS monohydrate are suspended in 900 ml of methyl ethyl ketone and heated to boiling. The mixture is stirred at boiling temperature for 10 min, cooled to room temperature and stirred at 20° C. for 2 h. The solid is filtered off with suction, washed with 120 ml of methyl ethyl ketone and dried in vacuo at 70° C.

Yield: 216.9 g of (1R,6S)-8-benzyl-7,9-dioxo-2,8-diazabicyclo[4.3.0]nonane-(−)-2,3:4,6-di-O-isopropylidene-2-keto-L-gulonic acid salt, 74.6% ee Filtrate: (1S,6R)-8-benzyl-7,9-dioxo-2,8-diazabicyclo[4.3.0]nonane (crude product which is partially present as (−)-2,3:4,6-di-O-isopropylidene-2-keto-L-gulonic acid salt) 84.6% ee.

Example 4

50 g (205 mmol) of cis-8-benzyl-7,9-dioxo-2,8-diazabicyclo[4.3.0]nonane are dissolved in 111 ml of methyl ethyl ketone (cloudy solution) and added dropwise in the course of 2 h to a boiling solution of 29.9 g of DAKS monohydrate in 139 ml of methyl ethyl ketone. The resulting suspension is stirred at boiling temperature for 10 min, cooled to room temperature and stirred at 20° C. for 2 h. The solid is filtered off with suction, washed with 80 ml of methyl ethyl ketone and dried in vacuo at 70° C.

Yield: 49.1 g (1R,6S)-8-benzyl-7,9-dioxo-2,8-diazabicyclo[4.3.0]nonane-(−)-2,3:4,6-di-O-isopropylidene-2-keto-L-gulonic acid salt.

The combined filtrates are treated with 9.7 ml of 37% strength hydrochloric acid and stirred at room temperature for 1 h. The resulting solid is filtered off with suction, washed with 50 ml of methyl ethyl ketone and dried in vacuo at 70° C.

Yield: 4.9 g cis-8-benzyl-7,9-dioxo-2,8-diazabicyclo[4.3.0]nonane hydrochloride (racemate)

The combined filtrates are adjusted to pH 10 using 8.5 ml of 25% strength ammonia solution, 36 ml of saturated sodium chloride solution are added, the organic phase is separated off and enriched, and the residue is dried in vacuo.

Yield: 22.0 g of (1S,6R)-8-benzyl-7,9-dioxo-2,8-diazabicyclo[4.3.0]nonane 99.6% ee.

Example 5

(1R,6S)-8-Benzyl-7,9-dioxo-2,8-diazabicyclo[4.3.0]nonane-(−)-2,3:4,6-di-O-isopropylidene-2-keto-L-gulonic Acid Salt.

2.0 kg (8.19 mol) of cis-8-benzyl-7,9-dioxo-2,8-diazabicyclo[4.3.0]nonane and 1.2 kg of (−)-DAKS×$H_2O$ [(−)-2,3:4,6-di-O-isopropylidene-2-keto-L-gulonic acid monohydrate] are heated under reflux for 30 min in 11.4 l of methyl ethyl ketone (MEK) and 0.57 l of water. The mixture is cooled to room temperature, and the crystallizate is filtered off with suction and washed with 3.2 l of MEK. The crystals are dried overnight at 70° C. in vacuo.

Yield: 1753 g of (1R,6S)-8-benzyl-7,9-dioxo-2,8-diazabicyclo[4.3.0]nonane-(−)-2,3:4,6-di-O-isopropylidene-2-keto-L-gulonic acid salt, 99.2% enantiomeric excess (ee).

Example 6

(1R,6S)-8-Benzyl-7,9-dioxo-2,8-diazabicyclo[4.3.0]
nonane-(1S)-camphorsulfonic Acid Salt x (1S)-camphorsulfonic acid 0.53 g (2.18 mmol) of cis-8-benzyl-7,9-dioxo-2,8-diazabicyclo[4.3.0]nonane (racemate) and 0.51 g (2.18 mmol) of (1S)-camphorsulfonic acid are dissolved in 30 ml of acetone under reflux to give a clear solution and cooled to room temperature. The precipitated solid is filtered off with suction and dried in vacuo to give 0.23 g (0.49 mmol) of (1R,6S)-8-benzyl-7,9-dioxo-2,8-diazabicyclo[4.3.0]nonane-(1S)-camphorsulfonic acid salt.

Enantiomeric excess: 88% ee

Yield: 42% of theory of (1R,6S)-8-benzyl-7,9-dioxo-2,8-diazabicyclo[4.3.0]nonane-(1S)-camphorsulfonic acid salt.

Example 7

(1R,6S)-8-Benzyl-7,9-dioxo-2,8-di azabicyclo[4.3.0]
nonane-(1S)-camphorsulfonic Acid Salt 0.52 g (2.12 mmol) of cis-8-benzyl-7,9-dioxo-2,8-diazabicyclo[4.3.0]nonane (racemate) and 0.49 g (2.12 mmol) of (1S)-camphor sulfonic acid are dissolved in 5 ml of acetonitrile under reflux to give a clear solution and cooled to room temperature. The precipitated solid is filtered off with suction and dried in vacuo to give 0.11 g (0.49 mmol) of (1R,6S)-8-benzyl-7,9-dioxo-2,8-diazabicyclo[4.3.0]nonane-(1S)-camphorsulfonic acid salt.

Enantiomeric excess: 96.6% ee

Yield: 22% of theory of (1R,6S)-8-benzyl-7,9-dioxo-2,8-diazabicyclo[4.3.0]nonane-(1S)-camphorsulfonic acid salt.

Example 8

(1R,6S)-8-Benzyl-7,9-dioxo-2,8-diazabicyclo[4.3.0]
nonane-(1S)-camphorsulfonic Acid Salt x (1S)-camphorsulfonic acid 4.8 g (10 mmol) of cis-8-benzyl-7,9-dioxo-2,8-diazabicyclo[4.3.0]nonane (racemate) and 2.36 g (5 mmol) of (1S)-camphorsulfonic acid are dissolved in 20 ml of acetonitrile under reflux to give a clear solution and cooled to room temperature. The precipitated solid is filtered off with suction and dried in vacuo to give 1.0 g (2.1 mmol) of (1R,6S)-8-benzyl-7,9-dioxo-2,8-diazabicyclo[4.3.0]nonane-(1S)-camphorsulfonic acid salt.

Enantiomeric excess: 99% ee

Yield: 21% of theory of (1R,6S)-8-benzyl-7,9-dioxo-2,8-diazabicyclo[4.3.0]nonane-(1S)-camphorsulfonic acid salt.

What is claimed is:

1. A process for the enrichment of enantiomers of cis-8-benzyl-7,9-dioxo-2,8-diazabicyclo[4.3.0]nonane, that comprises reacting mixtures of enantiomers of cis-8-benzyl-7,9-dioxo-2,8-diazabicyclo[4.3.0]nonane of the formula (I)

(I)

1R,6S          1S,6R with (−)-2,3:4,6-di-O-isopropylidene-2-keto-L-gulonic acid [or its hydrates] of the formula (II)

(II)

or its hydrates.

2. A process for the preparation of a mixture of enantiomers of the formula (I), that contains a molar excess of one of the two enantiomers, that comprises the process for the enrichment of enantiomers as claimed in claim 1.

3. A process for the preparation of (1S,6R)-8-benzyl-7,9-dioxo-2,8-diazabicyclo[4.3.0]nonane of the formula (Ia)

(Ia)

that comprises the process as claimed in claim 1.

4. A process for the preparation of (1S,6R)-8-benzyl-7,9-dioxo-2,8-diazabicyclo[4.3.0]nonane of the formula (Ib)

(Ib)

that comprises the process as claimed in claim 1.

5. The process as claimed in claims 1, 2, 3 or 4 which comprises releasing the amines from the (−)-2,3:4,6-di-O-isopropylidene-2-keto-L-gulonic acid salts using base.

6. The process as claimed in claim 5, in which the base is selected from the group which consists of sodium hydrogencarbonate and ammonia.

7. A (1S,6R)-8-benzyl-7,9-dioxo-2,8-diazabicyclo[4.3.0]nonane-(−)-2,3:4,6-di-O-isopropylidene-2-keto-L-gulonic acid salt of the formula

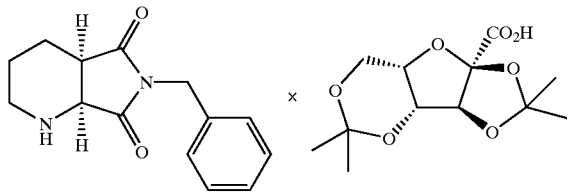

8. A (1R,6S)-8-benzyl-7,9-dioxo-2,8-diazabicyclo[4.3.0]nonane-(−)-2,3:4,6-di-O-isopropylidene-2-keto-L-gulonic acid salt of the formula

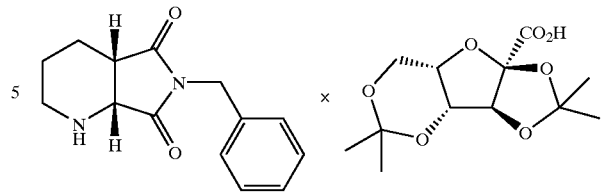

9. A mixture of the compounds as claimed in claims 7 and 8.

10. A process for the preparation of the compounds as claimed in claim 7, 8, or 9 which comprises the process as claimed in claim 1.

* * * * *